(12) United States Patent
Panchal et al.

(10) Patent No.: US 12,338,221 B2
(45) Date of Patent: *Jun. 24, 2025

(54) PROCESS FOR PREPARATION OF SULFENTRAZONE WITH TANK-MIX COMPATIBILITY

(71) Applicant: UPL LTD, Mumbai (IN)

(72) Inventors: Digish Manubhai Panchal, Mumbai (IN); Rakesh Bhikubhai Patel, Mumbai (IN)

(73) Assignee: UPL LTD, Mumbai (IN)

( * ) Notice: Subject to any disclaimer, the term of this patent is extended or adjusted under 35 U.S.C. 154(b) by 689 days.

This patent is subject to a terminal disclaimer.

(21) Appl. No.: 17/681,008

(22) Filed: Feb. 25, 2022

(65) Prior Publication Data

US 2022/0274937 A1    Sep. 1, 2022

(30) Foreign Application Priority Data

Feb. 26, 2021    (IN) ............................ 202121008116

(51) Int. Cl.
   *C07D 249/12*    (2006.01)
(52) U.S. Cl.
   CPC .................. *C07D 249/12* (2013.01)
(58) Field of Classification Search
   CPC .................................................. C07D 249/12
   See application file for complete search history.

(56) References Cited

U.S. PATENT DOCUMENTS

| | | | |
|---|---|---|---|
| 4,818,275 A * | 4/1989 | Theodoridis | A01N 43/653 504/273 |
| 5,990,315 A | 11/1999 | Dumas | |
| 9,440,932 B2 | 9/2016 | Framroze | |
| 11,447,455 B2 | 9/2022 | Nicholson et al. | |
| 11,634,392 B2 * | 4/2023 | Framroze | C07D 249/08 544/220 |
| 11,760,732 B2 * | 9/2023 | Panchal | C07D 249/12 548/243 |
| 11,827,897 B2 | 11/2023 | Van Rooijen et al. | |
| 2008/0139390 A1 | 6/2008 | Plant et al. | |
| 2010/0168177 A1 | 7/2010 | Qin et al. | |
| 2021/0032211 A1 | 2/2021 | Tu et al. | |
| 2022/0106277 A1 | 4/2022 | Framroze | |
| 2022/0274937 A1 | 9/2022 | Panchal et al. | |
| 2023/0046214 A1 | 2/2023 | Panchal et al. | |

FOREIGN PATENT DOCUMENTS

| | | | |
|---|---|---|---|
| IN | 2018/21018731 | * | 5/2018 |
| IN | 2018/21033380 | * | 9/2018 |
| IN | 201821018731 A | | 11/2019 |
| IN | 201821033380 A | | 3/2020 |
| WO | 2018/118621 | * | 6/2018 |
| WO | 2018118621 A1 | | 6/2018 |
| WO | 2019/141230 | * | 7/2019 |
| WO | 2019141230 A1 | | 7/2019 |

* cited by examiner

*Primary Examiner* — D Margaret M Seaman (74) *Attorney, Agent, or Firm* — CANTOR COLBURN LLP (57) ABSTRACT

Described herein is an environmentally friendly process for preparing pure sulfentrazone having tank-mix compatibility which includes treating sulfentrazone with a base and isolating the pure sulfentrazone with an acid. Compositions containing the pure sulfentrazone are also included.

8 Claims, 3 Drawing Sheets

PROCESS FOR PREPARATION OF SULFENTRAZONE WITH TANK-MIX COMPATIBILITY

CROSS-REFERENCE TO RELATED APPLICATIONS

This application claims priority to Indian Application 202121008116 filed on Feb. 26, 2021, which is incorporated herein by reference in its entirety.

FIELD OF THE DISCLOSURE

The present disclosure relates to an environmentally friendly process for preparing sulfentrazone having tank-mix compatibility.

BACKGROUND

Sulfentrazone is an herbicide belonging to the group of aryl triazolinones. It is chemically known as N[2,4-dichloro-5-[4-(difluoromethyl)-4,5-dihydro-3-methyl-5-oxo-1H-1,2,4-triazol-1-yl]phenyl]methanesulfonamide. It has high efficiency, low toxicity and a broad spectrum of action.

Sulfentrazone works by disrupting membranes and inhibiting photosynthesis in plants by a process referred to as protoporphyrinogen oxidase (PPO) inhibition. Sulfentrazone is received in the plants through the roots. After treatment with sulfentrazone, as the plants come out of the soil, they die after exposure to light. It is suitable for soybeans, corn, sorghum, peanut, sunflower and the like. It can control annual broad leaf weeds, grasses and sedges.

Very few processes for the preparation of sulfentrazone are known at this time. Conventionally, sulfentrazone is prepared as per process the provided in U.S. Pat. No. 4,818,275. However, the sulfentrazone obtained by such conventional processes does not have the desired purity and requires further purification.

Standard methods for the purification of organic molecules involve the use of silica gel column chromatography, use of multiple organic solvents, multiple recrystallization steps, or a combination of these processes. These standard processes are complicated, often involve use of large volumes of organic solvents, and are generally not suitable for large scale production.

The processes reported in literature for obtaining sulfentrazone employ organic solvents such as alcohols, which have a negative impact on the environment when with industrial scale processes. During the recovery of these solvents, there is loss of solvent which causes environmental pollution and also considerable economic loss.

Furthermore, it was observed that even after employing conventional methods for the purification of sulfentrazone, the final product obtained can include entrapped solvents, residual solvents, and is a mixture of multiple polymorphic forms of sulfentrazone. Formulations prepared using the sulfentrazone obtained by these conventional processes do not have the desired quality or satisfactory performance.

Another challenge arises when an end-user of sulfentrazone a formulation adds to the formulation, with dilution in water, a second agrochemical compound to form tank mixture. Such tank mixtures of sulfentrazone are widely used, but their use can be limited by the tendency of creaming of the active ingredient that can settle and clog the filters of nozzles of field spraying equipment. This tendency is further evidence of the physical incompatibility of conventionally prepared sulfentrazone in tank-mixtures.

To overcome above discussed problems, the inventors have consciously designed a highly desirable process for purification of sulfentrazone.

SUMMARY

According to an aspect of the present invention, there is provided an environmentally friendly process for preparing a sulfentrazone. The process provides sulfentrazone having tank-mix compatibility. In an aspect, the sulfentrazone prepared by the process described herein is essentially free of organic solvents and has a purity of greater than 98% as determined by HPLC. Advantageously, the sulfentrazone can be provided as a single component crystalline solid.

The process described herein provides a simple, industrially viable, reproduceable, environmentally friendly and cost-effective process for preparing sulfentrazone having tank-mix compatibility.

In an aspect, there is provided a process for preparing pure sulfentrazone which comprises treating a solid form of sulfentrazone with an aqueous base and isolating the pure sulfentrazone with an acid.

According to another aspect of, there provided a process for preparing pure sulfentrazone, comprising
  a) treating a solid form of sulfentrazone with an aqueous base to obtain a medium comprising a sulfentrazone salt;
  b) isolating the pure sulfentrazone by adjusting a pH of the medium with an acid.

According to another aspect, there is provided a process for preparing pure sulfentrazone, comprising,
  a) sulfonylating a compound of formula (II) to obtain a solid form of sulfentrazone of formula (I)

b) treating the solid form of sulfentrazone of formula (I) with an aqueous base to obtain a medium comprising a sulfentrazone salt;
  c) isolating the pure sulfentrazone by adjusting a pH of the medium with an acid.

According to another aspect, there is provided sulfentrazone having tank-mix compatibility.

According to another aspect, there is provided sulfentrazone essentially free of organic solvents.

According to yet another aspect, there is provided sulfentrazone essentially free of organic solvents having a purity of greater than 98% as determined by HPLC.

According to yet another aspect, there is provided sulfentrazone essentially free of organic solvents, further characterized by having a D90 particle size value of less than about 800 μm, preferably less than about 700 μm.

According to yet another aspect, there is provided sulfentrazone essentially free of organic solvents, further characterized by having a D50 particle size value of less than about 25 μm, preferably less than about 20 μm.

According to yet another aspect, there is provided sulfentrazone essentially free of organic solvents, is having bulk density of about 0.20 gm/ml to 0.70 gm/ml.

According to yet another aspect of the present invention, there is provided a salt of sulfentrazone and process for its preparation.

DESCRIPTION

Described herein is a process for preparing sulfentrazone which a) yields sulfentrazone having tank-mix compatibility; b) doesn't require the use of organic solvents; c) is adaptable to high production volumes; d) provides the product as a single component crystalline solid; and e) reduces the economic and environmental burden of the prior art processes.

Those skilled in art will be aware that invention described herein is subject to variations and modifications other than those specifically described. It is to be understood that the invention described herein includes all such variations and modifications. The invention also includes all such steps, features, compositions and methods referred to or indicated in this specification, individually or collectively, and any and all combinations of any two or more said steps or features.

Definitions

For convenience, before further description of the present invention, certain terms employed in the specification, examples are described here. These definitions should be read in light of the remainder of the disclosure and understood as by a person of skill in the art. Unless defined otherwise, all technical and scientific terms used herein have the same meaning as commonly understood by a person of ordinary skill in the art. The terms used throughout this specification are defined as follows, unless otherwise limited in specific instances.

The terms used herein are defined as follows.

The term "room temperature", unless stated otherwise, means a temperature in range of 20-35° C.

The term "purity" and "pure" refer to purity as determined by HPLC ("High Pressure Liquid Chromatography").

The term "salt" as used herein includes salts that can form with, for example, amines, ammonia, metals, alkali metals or alkaline earth metal bases or quaternary ammonium bases, including zwitter ions. Exemplary metal and alkaline earth metal hydroxides as salt formers include the salts of barium, aluminium, nickel, copper, manganese, cobalt zinc, iron, silver, lithium, sodium, potassium, magnesium or calcium.

As used herein the term "medium comprising sulfentrazone salt" unless stated otherwise, means a mixture comprising a liquid medium within which finely divided solids are dispersed, suspended or dissolved completely, the liquid medium may be entirely water, partially water, or may not contain any water at all. The term can be used interchangeably with slurry, dispersion or solution.

The term "solid form of sulfentrazone" as used herein can generically refer to any form of sulfentrazone from solvates, polymorphic forms, pseudo polymorph forms, amorphous forms, and mixtures thereof.

Also, the term "solid form of sulfentrazone" is used for sulfentrazone obtained from the conventional process is herein referred to as "technical sulfentrazone" and is used interchangeably. The solid form of sulfentrazone may have 1 to 10% wt/wt organic solvent content.

The term "pure sulfentrazone" as used herein refers to sulfentrazone obtained using the process described herein.

The term "sulfentrazone essentially free of organic solvent" as used herein means sulfentrazone containing less than 3% wt/wt of organic solvent content, specifically less than 1% wt/wt of organic solvent content, more specifically less than 0.5% of organic solvent content.

The term "creaming" as used herein refers to curding, coagulation, aggregation of solid particles, sedimentation, or flocculation.

The term "tank-mix compatibility" as used herein means that no adverse effects or physical incompatibility occurs as a result of mixing sulfentrazone with active pesticide/s or adjuvant/s in a tank-mix.

In the context of this invention, it was found that the sulfentrazone prepared by the conventional process presents with numerous problems such as a mixture of crystalline modification forms is obtained and/or organic solvent used during the chemical procedures gets trapped into such crystals. When such conventionally prepared sulfentrazone is used in the preparation of a tank-mix along with other agrochemicals, the tank-mix obtained has exhibits instability and has incompatibility issues.

The technique of tank mixing of various agrochemicals is well known and widely used as it saves time, labour and also reduces application costs. This technique which provides single application serves several purposes such as controlling pests and diseases, the application of foliar fertilizers, and the like. However, it was observed by the inventors that the conventionally prepared sulfentrazone, when used with other agrochemicals in a tank-mix, results in formation of large aggregates. These aggregates rapidly float to the surface, forming a layer, similar to a cream. This is also known commonly as "cream formation" or "creaming". This cream formation demonstrates that the conventionally prepared sulfentrazone shows incompatibility in tank-mix. Due to the creaming in the tank-mix solution, the solid particles formed settle and clog the filters of nozzles of field spraying equipment. Hence, along with the purity and other physiochemical properties, it is very important to produce an agrochemical which has compatibility with a wide range of other products and excipients. The compatibility of products is critical as incompatibility may cause serious problems such as loss of efficacy of some of the active ingredients, physical incompatibility between different compounds, separation, blocking of spray systems, foaming, crystallisation, and most importantly phytotoxicity.

The inventors made several attempts to remove trapped/residual organic solvent from sulfentrazone and to achieve a quality of sulfentrazone which has compatibility, however, the solution to this problem was either too expensive and resulted in decomposition of sulfentrazone or required the use of a large amount of organic solvent such as alcohols, which had an adverse impact on environment.

After systematic studies, the inventors found that the instability and incompatibility of conventionally obtained sulfentrazone can be overcome by a simple, environmentally friendly and cost-effective process. The inventors designed a process which does not require the use of any organic solvent or multiple recrystallizations.

According to an aspect, there is provided an environmentally friendly process for preparing pure sulfentrazone.

According to an aspect, there is provided a process for preparing pure sulfentrazone, which comprises treating a solid form of sulfentrazone with an aqueous base, and isolating the pure sulfentrazone with an acid.

According to an aspect, there is provided a process for preparing pure sulfentrazone, which comprises treating a solid form of sulfentrazone with an aqueous base, and isolating the pure sulfentrazone with an acid, wherein said process is carried out without use of an organic solvent.

In an embodiment, the solid form of sulfentrazone comprises any form of sulfentrazone, such as amorphous sulfentrazone or a mixture of different crystalline modifications or solvates of sulfentrazone or a mixture of amorphous and/or crystalline sulfentrazone and/or solvates of sulfentrazone.

In an embodiment, the solid form of sulfentrazone may contain organic solvents such as halogenated hydrocarbons like chlorobenzene, bromobenzene, dichlorobenzene, trifluoro methyl benzene and trichlorobenzene, ethers like diethyl ether, ethyl propyl ether, n-butyl ether, anisole, phenetole, cyclohexyl methyl ether, dimethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-tetrahydrofuran, polyethers of ethylene oxide and/or propylene oxide, nitrated hydrocarbons like nitromethane, nitroethane, nitropropane, nitrobenzene, chloronitrobenzene and ethyl benzene), aliphatic, cycloaliphatic or aromatic hydrocarbons like pentane, n-hexane, n-heptane, n-octane, nonane, cymene, petroleum fractions having a boiling range of from 70° C. to 190° C., cyclohexane, methylcyclohexane, petroleum ether, ligroin, octane, benzene toluene, xylene, dimethylbenzene, diethylbenzene, esters like malonates, n-butyl acetate, methyl acetate, ethyl acetate, isobutyl acetate, dimethyl carbonate, diethyl carbonate, dibutyl carbonate and ethylene carbonate, and aliphatic alcohols like methanol, ethanol, n-propanol, isopropanol, n-butanol and tert-amyl alcohol), mesitylene, diethyl ketone, methyl ethyl ketone, acetonitrile, and mixtures thereof.

In an embodiment, the base used to prepare pure sulfentrazone is selected from organic and inorganic bases.

In an embodiment, the base is an organic base such as methylamine, triethylamine, diethanolamine, piperidine, pyridine, and the like.

In another embodiment, the base is an inorganic base such as alkali or alkaline earth metal hydroxides, alkali metal or alkaline earth metal carbonates, alkaline earth metal oxides, p-block element carbonates, transition metal carbonates, ammonia and the likes.

Preferably, the base is selected from alkali or alkaline earth metal hydroxides, alkali metal or alkaline earth metal carbonates, alkaline earth metal oxides, p-block element carbonates, transition metal carbonates, ammonia or amines.

Basees such as sodium hydroxide, potassium hydroxide, silver hydroxide, ammonium hydroxide, barium hydroxide, magnesium hydroxide, calcium hydroxide, zinc hydroxide, iron(II) hydroxide, tin(II) hydroxide, lead(II) hydroxide, copper(II) hydroxide, Aluminium hydroxide, ferrous hydroxide, ammonia, lithium carbonate, lithium bicarbonate, sodium carbonate, sodium bicarbonate, potassium carbonate, potassium bicarbonate, magnesium carbonate, magnesium bicarbonate, calcium carbonate, calcium bicarbonate, barium carbonate, magnesium oxide, calcium oxide, barium oxide, thallium carbonate, lead carbonate, zinc carbonate, copper carbonate, silver carbonate, ferrous carbonate, and the like can be employed.

In another preferred embodiment, the base is selected from alkali metal carbonate such as lithium carbonate, lithium bicarbonate, sodium carbonate, sodium bicarbonate, potassium carbonate, potassium bicarbonate; or ammonia.

In an embodiment, the amount of base used with respect to sulfentrazone is in the range of 0.5 to 5 moles.

According to another embodiment, a method comprises treating the solid form of sulfentrazone with an aqueous base to obtain a medium comprising a sulfentrazone salt; and isolating pure sulfentrazone by adjusting a pH of the medium with an acid.

According to another embodiment of the present invention, treating the solid form of sulfentrazone with an aqueous base lead to formation of a medium comprising sulfentrazone salt.

According to another embodiment of the present invention, the step of treating the solid form of sulfentrazone with an aqueous base, may further comprise heating the medium to obtain a clear solution.

In an embodiment, the medium is heated at temperature in the range of about 40° C. to about 100° C.

According to another embodiment, the traces of solvent entrapped in the solid form of sulfentrazone can be recovered during heating of the medium.

According to an embodiment, the traces of solvent entrapped in the solid form of sulfentrazone can be recovered during azeotropic heating of the medium.

According to another embodiment, the clear solution obtained after heating the medium may be cooled before isolating the pure sulfentrazone. The clear solution may be cooled to below 40° C., preferably to room temperature or below.

According to an embodiment, the pure sulfentrazone is precipitated from the clear solution obtained without cooling.

According to another aspect, there is provided a process for preparing pure sulfentrazone, comprising
  a) treating a solid form of sulfentrazone with an aqueous base to obtain a medium comprising a sulfentrazone salt;
  b) isolating the pure sulfentrazone by adjusting a pH of the medium with an acid.

In an embodiment, the process is carried out in the absence of an organic solvent.

In an embodiment, the process is carried out in aqueous medium.

According to an embodiment, the solid form of sulfentrazone, upon treatment with aqueous base, results in formation of a medium comprising a sulfentrazone salt.

According to an embodiment, the sulfentrazone salt is an alkali metal salt, alkaline earth metal salt, salt of p-block elements, transition metal salt, or ammonium salt.

The sulfentrazone salt may be a sodium, potassium, silver, ammonium, barium, magnesium, calcium, zinc, iron, tin, lead, copper, aluminium, ferrous, lithium, thallium can be formed, preferably salt like sodium, potassium, calcium or ammonium salt.

According to an embodiment, the sulfentrazone salt obtained in above mentioned process may be isolated by any method known in the art, for example by evaporating the solvent so as to obtain a solid, or by forming a precipitate of the salt (e.g., by addition of an anti-solvent), and separating the precipitate from the reaction mixtures, e.g., by filtration.

According to another embodiment, the pure sulfentrazone is isolated by treatment with an acid.

According to yet another embodiment, the pure sulfentrazone is precipitated by adjusting the pH of the medium to 3 to 6, preferably 4 to 5 with an acid.

The adjustment of pH to obtain the product can be done by adding an acid to the medium comprising the sulfentrazone salt; or by adding the medium to an acid, however it was preferred to add the medium to an acid.

It was observed that, when acid is added to the medium comprising the salt, there may develop a problem of froth formation which makes the process cumbersome and tedious to handle. Hence, the preferred mode of addition is to add the medium to an acid.

The acid used for isolating the pure sulfentrazone is selected from an inorganic acid such as hydrochloric acid, sulfuric acid, nitric acid, phosphoric acid, boric acid, hydrofluoric acid, hydrobromic acid, perchloric acid, hydroiodic acid or an organic acid like acetic acid, formic acid, oxalic acid and the like, preferably hydrochloric acid.

In an embodiment, the amount of acid used with respect to sulfentrazone is in the range of 0.5 to 5 moles.

In an embodiment, there is provided a composition comprising pure sulfentrazone prepared by the process of the present disclosure, and at least one agrochemically acceptable excipient.

According to another embodiment, there is provided a sulfentrazone composition having tank-mix compatibility when mixed with one or more pesticide active compounds leading to a more uniform coverage of the pesticide active compounds on targeted plant surfaces.

According to an embodiment, there is provided a sulfentrazone composition having tank-mix compatibility when mixed with a second active ingredient.

In an embodiment of the present invention, the second active ingredient is selected from, but not limited to, an herbicide.

In an embodiment of the present invention, the herbicide used is selected from, but not limited to, an oxazole herbicide.

In an embodiment of the present invention, the oxazole herbicide used is clomazone.

According to yet another embodiment, the second pesticide active compound is in form of a formulation such as emulsifiable concentrate, soluble concentrate, suspension concentrate, and the like.

According to an embodiment, there is provided a sulfentrazone composition having tank-mix compatibility with one or more adjuvants.

According to an embodiment, the adjuvant used in tank mix is selected from, but not limited to, crop oil concentrates, vegetable oil, modified vegetable oil (typically esters such as soya methyl ester or salts of fatty acids), paraffin oil, mineral (petroleum) oils, surfactants, and inorganic salts or fertilizers.

In an embodiment, the tank-mix obtained using the composition comprising pure sulfentrazone prepared according to the present process is stable and demonstrates no sedimentation or creaming when mixed with another agrochemical active composition.

According to another aspect, there is provided pure sulfentrazone essentially free of organic solvents.

According to yet another aspect, there is provided pure sulfentrazone essentially free of organic solvents having purity of greater than 98% as determined by HPLC.

According to yet another aspect, there is provided pure sulfentrazone essentially free of organic solvents, further characterized by having a D90 particle size value of less than about 800 μm, preferably less than about 700 μm.

According to yet another aspect, there is provided pure sulfentrazone essentially free of organic solvents, further characterized by having a D50 particle size value of less than about 25 μm, preferably less than about 20 μm.

According to yet another aspect, there is provided pure sulfentrazone essentially free of organic solvents, having a bulk density of about 0.20 gm/ml to 0.70 gm/ml.

According to yet another aspect, the pure sulfentrazone obtained is in single polymorphic form.

According to yet another aspect, there is provided a salt of sulfentrazone and process for its preparation.

In an embodiment, the salt of sulfentrazone obtained is a sodium salt.

According to an embodiment, there is provided a process for preparing pure sulfentrazone having tank-mix compatibility, comprising
a) treating a solid form of sulfentrazone with an aqueous alkali metal carbonate to obtain a medium comprising a sulfentrazone salt; and
b) isolating the pure sulfentrazone having tank-mix compatibility by adjusting a pH of the medium to 3 to 6 with an acid, such as hydrochloric acid.

The solid form of sulfentrazone used as starting material can be prepared conventionally by methods known in the art. For an instance, the solid form of sulfentrazone used as starting material in the present invention may be prepared by sulfonylating a compound of formula (II).

Formula (II)

One of the methods for preparing the sulfentrazone formula (I) involves sulfonylation, which is done by reacting compound of formula (II) with methane sulfonyl chloride in presence of a solvent such as toluene and a catalyst such as pyridine.

Formula (II)

Formula (I)

According to another aspect, there is provided a process for preparing pure sulfentrazone having tank-mix compatibility,
comprising,
a) sulfonylating a compound of formula (II) to obtain solid form of sulfentrazone of formula (I)

Formula (II)

Formula (I)

b) treating the sulfentrazone of a) with an aqueous base to obtain a medium comprising a sulfentrazone salt;
c) isolating the pure sulfentrazone having tank-mix compatibility by adjusting a pH of the medium with an acid.

In an embodiment, in step a), compound of formula (II) is sulfonylated to obtain sulfentrazone of formula (I).

The sulfonylating agent used in step a) is methane sulfonyl chloride.

The step a) may be carried out by reacting the compound of formula (II) with methane sulfonyl chloride in the presence of a catalyst and a solvent at temperature ranging from 50° C. to 160° C.

The amount of methane sulfonyl chloride used with respect to compound of formula (II) is in the range of 0.5 to 2 moles.

The catalyst used is selected from an inorganic or organic base. An organic base such as alkylamine (as tertiary amine base etc.), pyridine, picoline, quinoline, quinuclidine, phosphazene, imidazole, benzimidazole and the like, may be employed.

The amount of catalyst used with respect to compound of formula (II) is in the range of 0.05 to 0.5.

Exemplary solvents include halogenated hydrocarbons such as chlorobenzene, bromobenzene, dichlorobenzene, trifluoro methyl benzene and trichlorobenzene, ethers like diethyl ether, ethyl propyl ether, n-butyl ether, anisole, phenetole, cyclohexyl methyl ether, dimethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-tetrahydrofuran, polyethers of ethylene oxide and/or propylene oxide, nitrated hydrocarbons like nitromethane, nitroethane, nitropropane, nitrobenzene, chloronitrobenzene and ethyl benzene), aliphatic, cycloaliphatic or aromatic hydrocarbons like pentane, n-hexane, n-heptane, n-octane, nonane, cymene, petroleum fractions having a boiling range of from 70° C. to 190° C., cyclohexane, methylcyclohexane, petroleum ether, ligroin, octane, benzene toluene, xylene, dimethylbenzene, diethylbenzene, esters like malonates, n-butyl acetate, methyl acetate, ethyl acetate, isobutyl acetate, dimethyl carbonate, diethyl carbonate, dibutyl carbonate and ethylene carbonate, and aliphatic alcohols like methanol, ethanol, n-propanol, isopropanol, n-butanol and tert-amyl alcohol), mesitylene, diethyl ketone, methyl ethyl ketone, acetonitrile, and mixtures thereof.

Figure 1:
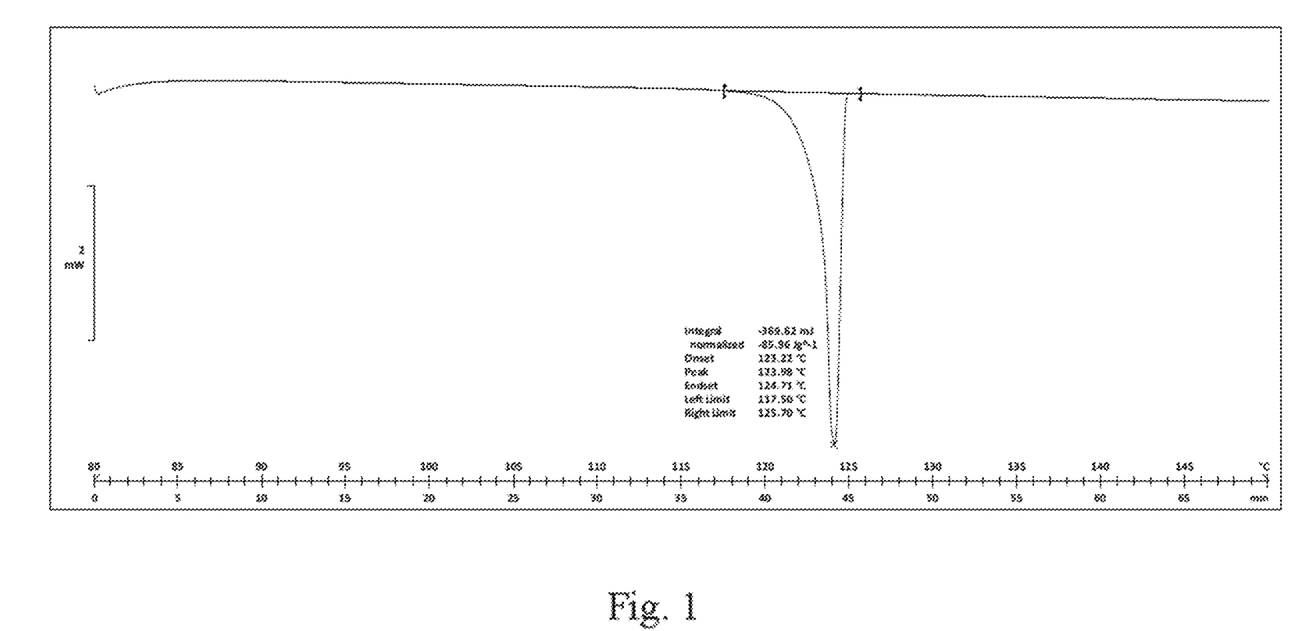
FIG. 1 depicts a differential scanning calorimetric (DSC) thermogram of pure sulfentrazone having tank-mix compatibility obtained by the process provided herein.

According to an embodiment, the sulfentrazone is characterized by a differential scanning calorimetric (DSC) thermogram having an endotherm at about 123° C. to 125° C.

The pure sulfentrazone having tank-mix compatibility obtained in accordance to the present disclosure is characterized by differential scanning calorimetric (DSC) thermogram represented by FIG. 1.

EXAMPLES

The following examples are presented to provide what is believed to be the most useful and readily understood description of procedures and conceptual aspects of this invention. The examples provided below are merely illustrative of the invention and are not intended to limit the same to disclosed embodiments. Variations and changes obvious to one skilled in the art are intended to be within the scope and nature of the invention.

Methods

Differential Scanning Calorimetry (DSC):

DSC thermogram was measured by a Differential scanning calorimeter (DSC 822, Mettler Toledo) with heating rates of 1, 2 or 5°/min in the range from 30° C. to 200° C.

HPLC Conditions:
- Column: Cosmosil® 5C1 8 (4.6×250 mm×5 micron)
- Mobile Phase: 0.1% H3PO4 in water: Acetonitrile (50:50)
- Dilution System: Acetonitrile
- Flow: 1.0 ml/min
- UV-Wavelength: 210 nm
- Injection volume: 3.0 μl
- Column temperature: 40° C.
- Run time: 40 min Example 1: Preparation of Solid Sulfentrazone Sulfentrazone (formula (I)) can be prepared by processes as described in U.S. Pat. Nos. 4,818,275, 5,990,315 or any of the method known in prior art, one of such known method is provided below.

Compound of formula (II) (466 g) was taken in toluene (751 g) and heated to 110° C.±2° C. to which pyridine (11 g) and methanesulfonyl chloride (204 g) were added and the reaction mixture was maintained at said temperature for 12 hours. After completion of reaction, toluene (2778 g) was added at 110° C.±2° C. The mixture was cooled to room temperature and to it was added water (262 g) and 20% sodium carbonate solution (41 g). The mixture was then cooled to 5 to 10° C., filtered and washed with chilled toluene to yield 728 g of wet cake comprising solid sulfentrazone of formula (I).

Formula (II)

Formula (I)

Example 2: Process for Preparing Pure Sulfentrazone Having Tank-Mix Compatibility Step A A solution of sodium carbonate (2040 g, 5%) was heated to about 70° C. followed by the addition of the wet cake (728 g) obtained in Example 1. The mixture was then heated to 80-85° C. and maintained for 1 hour to provide a clear solution. The clear solution obtained was cooled to room temperature to provide a slurry comprising a sodium salt of sulfentrazone.

Step B

The slurry comprising the sodium salt of sulfentrazone of step a) was added to dilute hydrochloric acid (703 g, 10%) at room temperature and the pH of mixture was adjusted to 4-5. The mixture was maintained at 30-35° C. for another hour and then filtered through a Buckner funnel. The wet cake was washed with hot water and was dried in oven to remove moisture to provide 485 g (97.97% yield) of pure sulfentrazone having HPLC purity of 98.2% (wt/wt).

Particle Size Distribution: D10=1.84 μm; D50=17.1 μm and D90=652 μm

Bulk density: 0.3270 gm/ml

Toluene Content: less than 0.1%

The DSC thermogram exhibited an endothermic melting peak with onset at 123.22° C. and peak maximum at 123.98° C.

Example 3: Process for Preparing Pure Sulfentrazone Having Tank-Mix Compatibility Step A A solution of potassium carbonate (428 g, 5%) was heated to about 70° C. followed by the addition of the wet cake (100 g) obtained as in Example 1. The mixture was then heated to 80-85° C. and maintained for 1 hour to provide a clear solution. The clear solution obtained was cooled to room temperature to provide a medium comprising a potassium salt of sulfentrazone.

Step B

The medium comprising the potassium salt of sulfentrazone of step a) was added to dilute hydrochloric acid (113 g, 10%) at room temperature and the pH of mixture was adjusted to 4-5. The mixture was maintained at 30-35° C. for another hour and then filtered. The wet cake was washed with hot water and was dried in oven to remove moisture to provide 80 g (97.5% yield) of pure sulfentrazone having HPLC purity of 98% (wt/wt).

Example 4: Process for Preparing Pure Sulfentrazone Having Tank-Mix Compatibility Step A A solution of sodium hydroxide (248 g, 5%) was heated to about 70° C. followed by the addition of the wet cake (100 g) obtained as in Example 1. The mixture was then heated to 80-85° C. and maintained for 1 hour to provide a clear solution. The clear solution obtained was cooled to room temperature to provide a medium comprising a sodium salt of sulfentrazone.

Step B

The medium comprising the sodium salt of sulfentrazone of step a) was added to dilute hydrochloric acid (113.8 g, 10%) at room temperature and the pH of mixture was adjusted to 4-5. The mixture was maintained at 30-35° C. for another hour and then filtered. The wet cake was washed with hot water and was dried in oven to remove moisture to provide 60 g (75% yield) of pure sulfentrazone having HPLC purity of 94.6% (wt/wt).

Example 5: Process for Preparing Pure Sulfentrazone Having Tank-Mix Compatibility Step a A solution of ammonia (106 g) was heated to about 80° C. followed by the addition of the wet cake (100 g) obtained as in Example 1. The mixture was then heated to 85-90° C. and maintained for 1 hour to provide a clear solution. The clear solution obtained was cooled to room temperature to provide a medium comprising an ammonium salt of sulfentrazone.

Step B

The medium comprising the ammonium salt of sulfentrazone of step a) was added to dilute hydrochloric acid (113.8 g, 10%) at room temperature and the pH of mixture was adjusted to 4-5. The mixture was maintained at 30-35° C. for another hour and then filtered. The wet cake was washed with hot water and was dried in oven to remove moisture to provide 79 g (96.6% yield) of pure sulfentrazone having HPLC purity of 98% (wt/wt).

Example 6

Using the standard method, a suspension concentrate formulation of sulfentrazone was prepared. The composition of the formulation is as given below:

| Sr. No. | Ingredients | Quantity (% w/w) |
| --- | --- | --- |
| 1 | Sulfentrazone prepared according to example 2 | 42.25 |
| 2 | Polyoxyethylene tristerylphenol phosphate, potassium salt | 3.70 |
| 3 | Sodium alkylnaphthalenesulfonate, formaldehyde condensate | 1.00 |
| 4 | Monoetylene glycol | 5.00 |
| 5 | Magnesium aluminosilicate | 0.60 |
| 6 | Polydimethylsiloxane | 0.50 |
| 7 | Xanthan gum | 0.16 |
| 8 | 1,2-Benzoisothiazolin-3-one | 0.10 |
| 9 | Water | QS |

Example 7: Comparative Example

A suspension concentrate formulation of using the solid sulfentrazone prepared according to Example 1 was prepared; the remaining ingredients of the of formulation are same as that of example 6.

Performance Evaluation

Samples (Sample 1 and 2) prepared according to Example 6 and Example 7 were tested for performance. Physicochemical properties of ambient (0 days) and AHS (14 days) sample were checked as per CIPAC method. The observation was recorded as below:

| | | | Sample 1 | | Sample 2 | |
| --- | --- | --- | --- | --- | --- | --- |
| Sr. No. | Performance parameters | Specification | 0 Days | 14 Days AHS | 0 Days | 14 Days AHS |
| 1 | Appearance | White to off-white colour suspension | Complies | Complies | Complies | Complies |
| 2 | Active Content (gm/L) | 475 to 525 | 516.88 | 511.24 | 501.06 | 498.61 |
| 3 | Suspensibility on active bases (% w/w) | Min 80.0 | 99.0 | 97.62 | 97.3 | 96.61 |
| 4 | Wet Sieve Test (Material retention) | 0.20% max on 45 µm 0.05% max on 150 µm | Nil | Nil | Nil | Nil |
| 5 | Persistence foam (After 1 min) | 15 ml | Nil | Nil | Nil | Nil |

Tank Mix Compatibility Test

I) With Other Pesticide Active Compound

Samples prepared according to Example 6 and Example 7 were tested for compatibility with clomazone EC formulation (UPSTAGE®). The tank mix compatibility was checked as per the dosages mentioned below:

| Product to be used in tank mix | Active Ingredient | Concentration (gm/L) | Field dilution (Dosage in L/Ha) | Spraying Volume (L/Ha) |
| --- | --- | --- | --- | --- |
| Sample 1 (prepared according to Example 6) | Sulfentrazone in accordance with example 2 | 500 SC | 1.4 | 50 |
| Sample 2 (prepared according to Example 7) | Sulfentrazone prepared in accordance with Example 1 | 500 SC | 1.4 | |
| UPSTAGE® | Clomazone | 500 EC | 2.0 | |

Method: Total 250 ml of spray dilution solution was prepared using above mentioned composition wherein 7 ml of each sample 1 and sample 2 were mixed with 10 ml of UPSTAGE® and mixture was diluted with water.

Following observations were made:

| Sample No | Observation | Result |
| --- | --- | --- |
| Sample 1 with UPSTAGE® | No creaming observed after 3 hrs. There is very little, or no sediment observed when emulsion was passed through 60, 100 and 325 mesh size sieves (Refer FIG. 2) | Compatible in tank mix test with Up-stage. |
| Sample 2 with Up-stage | Creaming observed after 3 hrs. There were lot of sediment found on the sieve when tank mix solution was passed through 60, 100 and 325 mesh size sieves. (Refer FIG. 3) | Not compatible in tank mix test with Up-Stage. |

Figure 3:
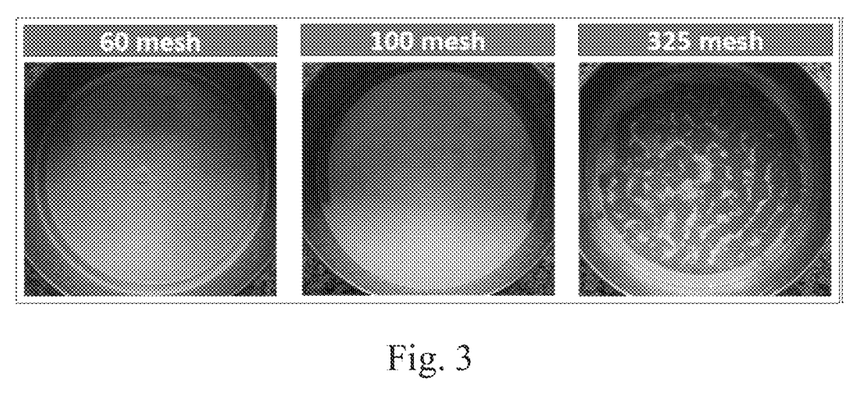
FIG. 3 is a photograph showing results of a tank mix compatibility test for sample 2.

Conclusion: The conventionally prepared sulfentrazone exhibited moderate to severe physical incompatibilities when mixed with a clomazone EC formulation (FIG. 3). The physical incompatibilities were in the form of moderate to severe creaming followed by settling and eventually resulting in formation of large aggregates. The severity of the incompatibility would clog filters of nozzles of field spraying equipment and would likely affect the proper distribution of this herbicide during the application.

Whereas the sulfentrazone prepared in accordance with the present disclosure, when mixed with a clomazone EC formulation did not result in any physical incompatibilities (FIG. 2) and proved to be compatible.

Figure 2:
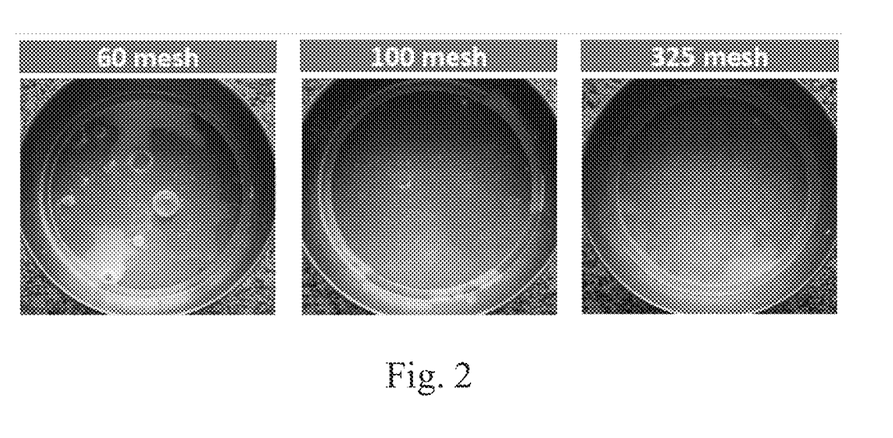
FIG. 2 is a photograph showing results of a tank mix compatibility test for sample 1.

FIG. 2 is a photograph showing results of the tank mix compatibility test for sample 1.

FIG. 3 is a photograph showing results of the tank mix compatibility test for sample 2.

II) With Adjuvants

Samples were prepared according to Example 6 and were tested for compatibility with soya methyl ester (Strides). The tank mix compatibility was checked as per the dosages mentioned below:

| Product to be used in tank mix | Active Ingredient | Concentration (gm/L) | Field dilution (Dosage in L/Ha) | Spraying Volume (L/Ha) |
|---|---|---|---|---|
| Sample 3 (prepared according to Example 6) | Sulfentrazone in accordance with example 2 | 500 SC | 1.4 | 50 |
| Strides | Soya Methyl Ester | 720 | 0.25 | 50 |

Method: Total 250 ml of spray dilution solution was prepared using above mentioned dilution wherein 7 ml of sample 3 were mixed with 1.25 ml Strides and mixture was diluted with water.

Following observations were made:

| Sample No | Observation | Result |
|---|---|---|
| Sample 3 with Strides | There is no flocculation/ coagulation observed in dilution mixture after 3 hrs | Compatible in tank mix test with strides. |

The invention claimed is:

1. Sulfentrazone essentially free of organic solvents having:

purity of greater than 98% by HPLC;

$D_{50}$ particle size of less than about 25 μm; and bulk density of about 0.20 gm/ml to 0.70 gm/ml.

2. A composition comprising the sulfentrazone of claim 1, and at least one agrochemically acceptable excipient.

3. The composition as claimed in claim 2, wherein said composition has tank-mix compatibility with at least one oxazole herbicide.

4. The composition as claimed in claim 3, wherein said oxazole herbicide is clomazone.

5. The composition as claimed in claim 2, wherein said composition has tank-mix compatibility with one or more adjuvants selected from crop oil concentrates, vegetable oil, modified vegetable oil, paraffin oil, mineral oils, surfactants, inorganic salts, or fertilizer.

6. The sulfentrazone of claim 1, having an endotherm at about 123 to 125° C., as measured by differential scanning calorimetry (DSC).

7. The sulfentrazone of claim 1, having a toluene content of less than 0.1% by weight.

8. The composition of claim 4, exhibiting tank-mix compatibility, as measured by visual observation of very little or no sediment when said composition is passed through 60, 100, and 325 mesh size sieves.

* * * * *